US008192355B2

(12) United States Patent
Jacob

(10) Patent No.: US 8,192,355 B2
(45) Date of Patent: Jun. 5, 2012

(54) ENDOLUMINAL COLOSTOMY SYSTEM AND PROCEDURE

(75) Inventor: Brian P. Jacob, New York, NY (US)

(73) Assignee: Mount Sinai School of Medicine, New York, NY (US)

(*) Notice: Subject to any disclaimer, the term of this patent is extended or adjusted under 35 U.S.C. 154(b) by 859 days.

(21) Appl. No.: 10/798,246

(22) Filed: Mar. 10, 2004

(65) Prior Publication Data

US 2004/0225277 A1  Nov. 11, 2004

Related U.S. Application Data

(60) Provisional application No. 60/453,580, filed on Mar. 11, 2003.

(51) Int. Cl.
*A61B 1/00* (2006.01)
(52) U.S. Cl. .................................. 600/184; 606/108
(58) Field of Classification Search .................. 600/184, 600/114, 128, 129, 135, 139, 201, 203, 204, 600/206, 585; 606/185, 170, 171, 108; D24/108, D24/112, 106; 604/164.01; 623/6.12
See application file for complete search history.

(56) References Cited

U.S. PATENT DOCUMENTS

| 5,071,408 | A | * | 12/1991 | Ahmed | 606/108 |
|---|---|---|---|---|---|
| 5,312,351 | A | * | 5/1994 | Gerrone | 604/117 |
| 5,360,414 | A | * | 11/1994 | Yarger | 604/264 |
| 5,380,290 | A | * | 1/1995 | Makower et al. | 604/164.01 |
| 5,400,768 | A | * | 3/1995 | McNamara et al. | 600/104 |
| 5,599,304 | A | * | 2/1997 | Shaari | 604/94.01 |
| 6,517,518 | B2 | * | 2/2003 | Nash et al. | 604/164.02 |

* cited by examiner

*Primary Examiner* — Ryan Severson
(74) *Attorney, Agent, or Firm* — Fish & Richardson P.C.

(57) ABSTRACT

A trocar for positioning within a body lumen such as an intestine is disclosed. The trocar has a window adjacent its distal end in communication with the internal lumen of the trocar. The trocar is sufficient rigid to stabilize the body lumen upon positioning therein to maintain patency of the body lumen. A slot in communication with the window extends to the distal end of the trocar.

A surgical procedure for reversing a colostomy procedure is also disclosed. The above described trocar is inserted into a first intestinal section through an opening in the abdominal wall. A guide wire is introduced through the rectal opening and advanced through the rectal stump and out the opening in the abdominal wall. An anvil is connected to the guide wire and the guide wire withdrawn through the rectal opening to advance the anvil within the first intestinal section. An anastomosis instrument is introduced through the rectal opening and connected to the anastomosis instrument. The anastomosis instrument is fired to connect the two intestinal sections to reestablish continuity between them.

19 Claims, 10 Drawing Sheets

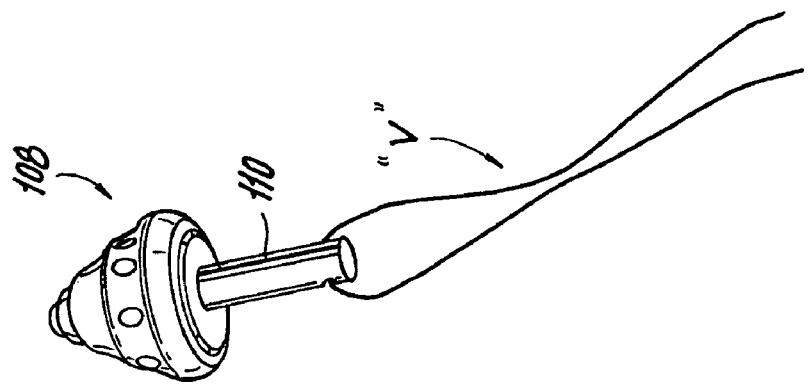
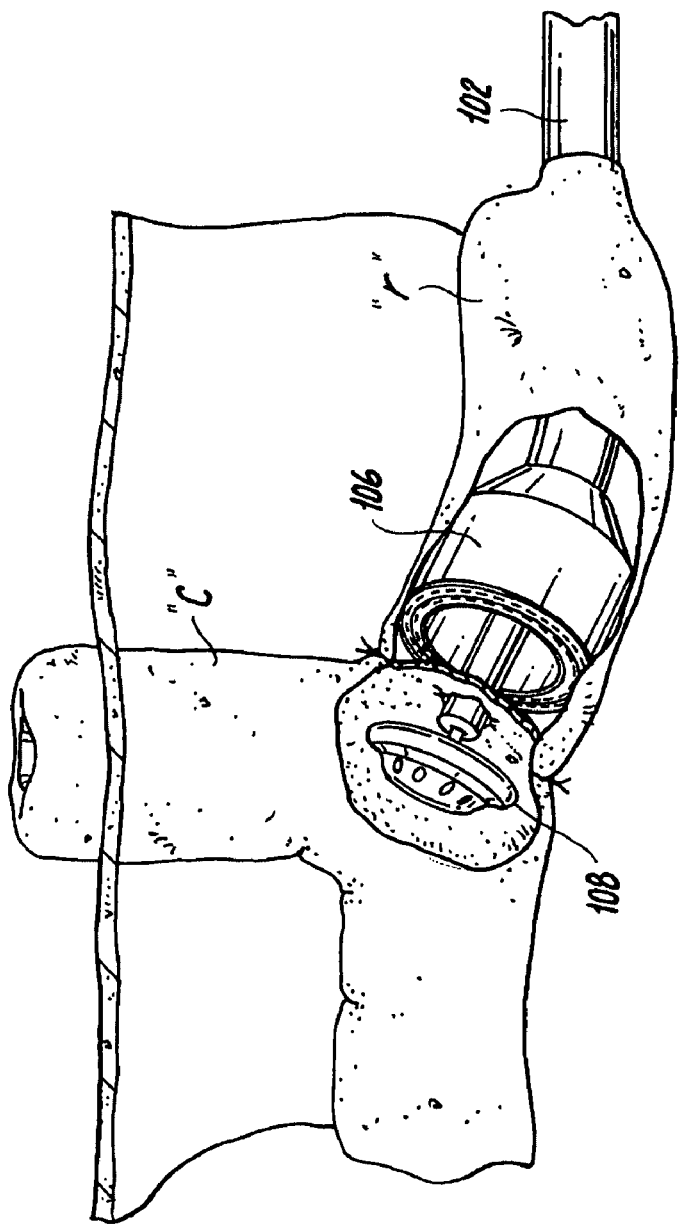

ENDOLUMINAL COLOSTOMY SYSTEM AND PROCEDURE

This application claims priority pursuant to 35 U.S.C. 119 based upon U.S. Provisional Patent Application Ser. No. 60/453,580 filed Mar. 11, 2003, the entire disclosure of which is hereby incorporated by reference.

FIELD OF THE DISCLOSURE

The present invention relates to a colostomy procedure and, more particularly, to a method for performing an endoluminal colostomy reversal procedure and a device for use in the procedure.

DESCRIPTION OF THE PRIOR ART

A colostomy is a surgical procedure in which a portion of a large intestine or colon is brought through the abdominal wall to provide an alternate conduit to carry feces from the body. A colostomy is established to treat various disorders of the large intestine including cancer, obstruction, inflammatory bowel disease, etc. Colostomies may be temporary or permanent.

A typical colostomy procedure is an end colostomy. An end colostomy involves the removal of a diseased portion of the intestinal tract. The healthy or functioning end of the intestine, i.e., which remains connected to the upper gastro intestinal tract, is brought out of the skin of the abdominal wall where it is sutured in place to create an opening or stoma in the surface of the body. An adhesive drainage (stoma appliance) may be placed around the opening. Thereafter, the distal portion of the bowel which is connected to the rectum may be removed or, in the alternative, closed via suturing and left in the abdomen.

Depending on the disease process being treated, the colostomy may be reversed within weeks or months after the first operation to reestablish a normal gastrointestinal path through the rectum. However, known techniques and associated devices for, effecting colostomy reversal are relatively invasive resulting in increased trauma to the patient and/or an increased morbidity and mortality rate.

SUMMARY

Accordingly, the present disclosure is directed to an apparatus and associated procedure for reversing a colostomy procedure. The preferred apparatus advantageously limits the invasiveness of this second stage reversal procedure. In one preferred embodiment, an access device for positioning within a body lumen such as an intestine is disclosed. The access device includes an access member having an outer wall defining an internal lumen. The access member defines a longitudinal axis and proximal and distal ends. The outer wall has a window adjacent the distal end in communication with the internal lumen. The access member has a cross-sectional dimension transverse to the longitudinal axis and a rigidity sufficient to stabilize the body lumen upon positioning therein to maintain patency of the body lumen. The outer wall may define a slot in communication with the window and extending to the distal end of the access member.

A novel surgical procedure for reversing a colostomy procedure of the type where an intestinal section is resected leaving a first intestinal section which is attached adjacent an opening in the abdominal wall and a second intestinal section which extends to a rectal opening is disclosed. The procedure incorporates the aforedescribed access device. The procedure includes the steps of:

accessing a first intestinal section through the opening in the abdominal wall;

introducing a guide within the rectal opening and advancing the guide through the second intestinal section and out the opening in the abdominal wall;

connecting an anvil to the guide;

withdrawing the guide through the rectal opening to advance the anvil within the first intestinal section;

introducing an anastomosis instrument within the rectal opening and into the second intestinal section and connecting the anvil to the anastomosis instrument; and firing the anastomosis instrument to connect the first and second intestinal sections to re-establish continuity between the first and second intestinal sections.

Preferably the first intestinal section is accessed with an access device which is positioned through the opening in the abdominal wall and advanced within the first intestinal section. The guide is advanced through the lumen of the access device and out the opening in the abdominal wall. Thereafter the access device may be removed.

The procedure may be visualized with endoscopes positioned through trocars accessing the abdominal cavity and/or with scopes introduced within the access device and rectal opening.

BRIEF DESCRIPTION OF THE DRAWINGS

The foregoing features of the present disclosure will become more readily apparent and will be better understood by referring to the following detailed description of preferred embodiments, which are described hereinbelow with reference to the drawings wherein:

FIGS. 5-10 are views illustrating the sequence of steps in performing an endoluminal procedure for colostomy reversal in accordance with the preferred method of the present disclosure.

DETAILED DESCRIPTION OF THE PREFERRED EMBODIMENTS

The preferred embodiments of the system and surgical procedure disclosed herein are discussed in terms of a colostomy reversal procedure in the digestive system, and devices utilized to carry out the procedure.

The following discussion will include a description of each instrument or device utilized in performing the colostomy reversal procedure followed with a description of a preferred method for performing the colostomy reversal in accordance with the principles of the present disclosure.

In the discussion which follows, the term "proximal", as is traditional will refer to the portion of the structure which is closest to the operator while the term distal will refer to the portion which is furthest from the operator.

Figure 1:
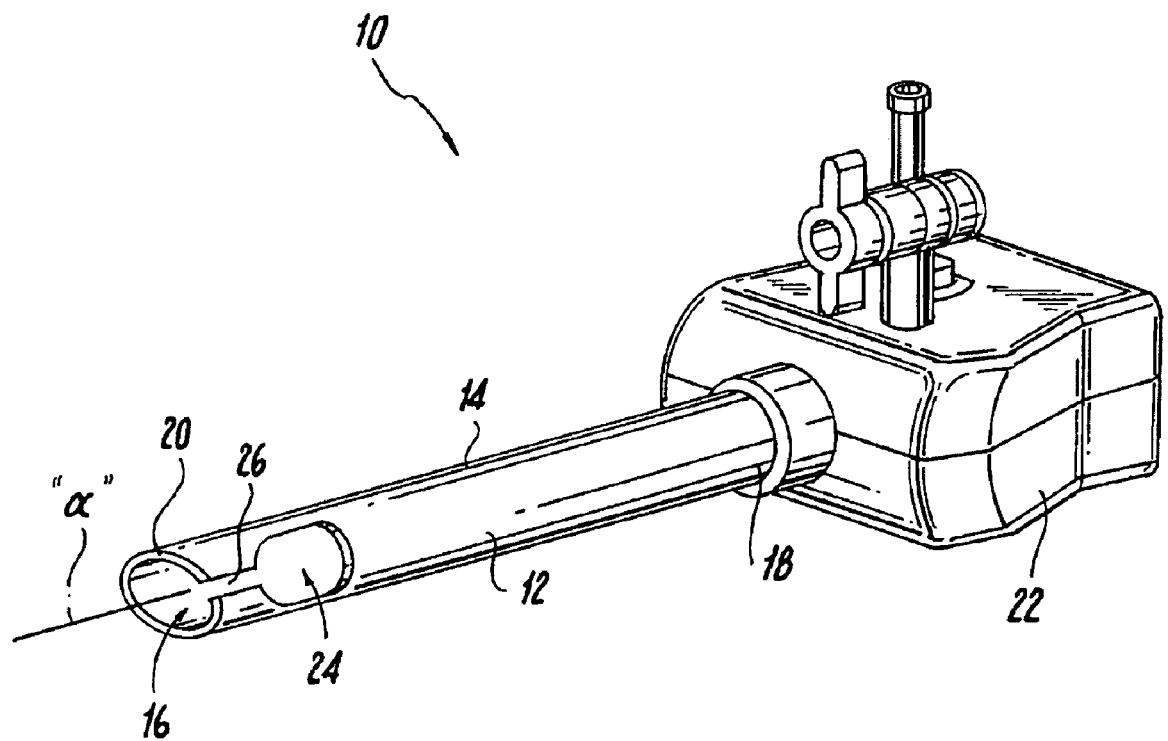
FIG. 1 is a perspective view of an access device of the system to be utilized in performing the novel endoluminal procedure for colostomy reversal in accordance with the principles of the present disclosure.

Referring now to FIG. 1, there is illustrated a preferred embodiment of an instrument or device of the system for performing an endoluminal colostomy reversal procedure in accordance with the principles of the present disclosure. A trocar or access device 10 includes an elongated access member 12 having an outer wall 14 which defines a longitudinal axis "a". Outer wall 14 encloses longitudinal bore 16 which extends the length of the access member 12, i.e., from proximal end 18 to distal end 20 of the access member 12 and into a lumen of the large intestine. Access device 10 preferably has sufficient rigidity to be advanced through an abdominal opening. Suitable materials of fabrication include preferably medical grade material inclusive of medical grade polymeric materials, stainless steel, titanium or any other suitable metal. Alternatively, access device may be flexible to permit navigation through a potentially tortuous path through tissue. In a preferred embodiment, access device 10 includes a trocar or cannula sleeve which may or may not include a cannula housing 22 shown in FIG. 1. The cannula sleeve defines an outer wall encircling the longitudinal passageway and a longitudinal bore extending through the sleeve. The diameter of the cannula sleeve preferably ranges from about 2 mm (millimeters) to about 20 mm, more preferably from about 5 mm to about 12 mm. If equipped, the cannula housing 22 provides a housing or handle dimensioned to facilitate manipulation of the access device 10 about the surgical site.

Access member 12 or cannula sleeve has a window 24 in its outer wall 14 spaced from distal end 20. Window 24 communicates with longitudinal bore 16 of access member 12 and is advantageously dimensioned to receive instrumentation therein during performance of the surgical procedure. Window 24 also permits visualization of the operative site. Preferably, window 24 defines a radial arc ranging from about 90 degrees to about 180 degrees about longitudinal axis "a" of the access member 12. Access member 12 may further include a slot 26 which extends from distal end 20 to window 24. Slot 26 facilitates removal of a surgical instrument and/or access, member 12 during the procedure as will be discussed.

Access device 10 acts as both a mucosal protection and lumen stabilizing device for the anastomosis site. The endoluminal trocar serves several purposes. Besides increasing precision for locating and visualizing the zone of safety within the future ostomy site, the tube stabilizes the future anastomosis site, permits a precise needle puncture, and protects the opposite luminal wall from inadvertent injury.

Figure 2:
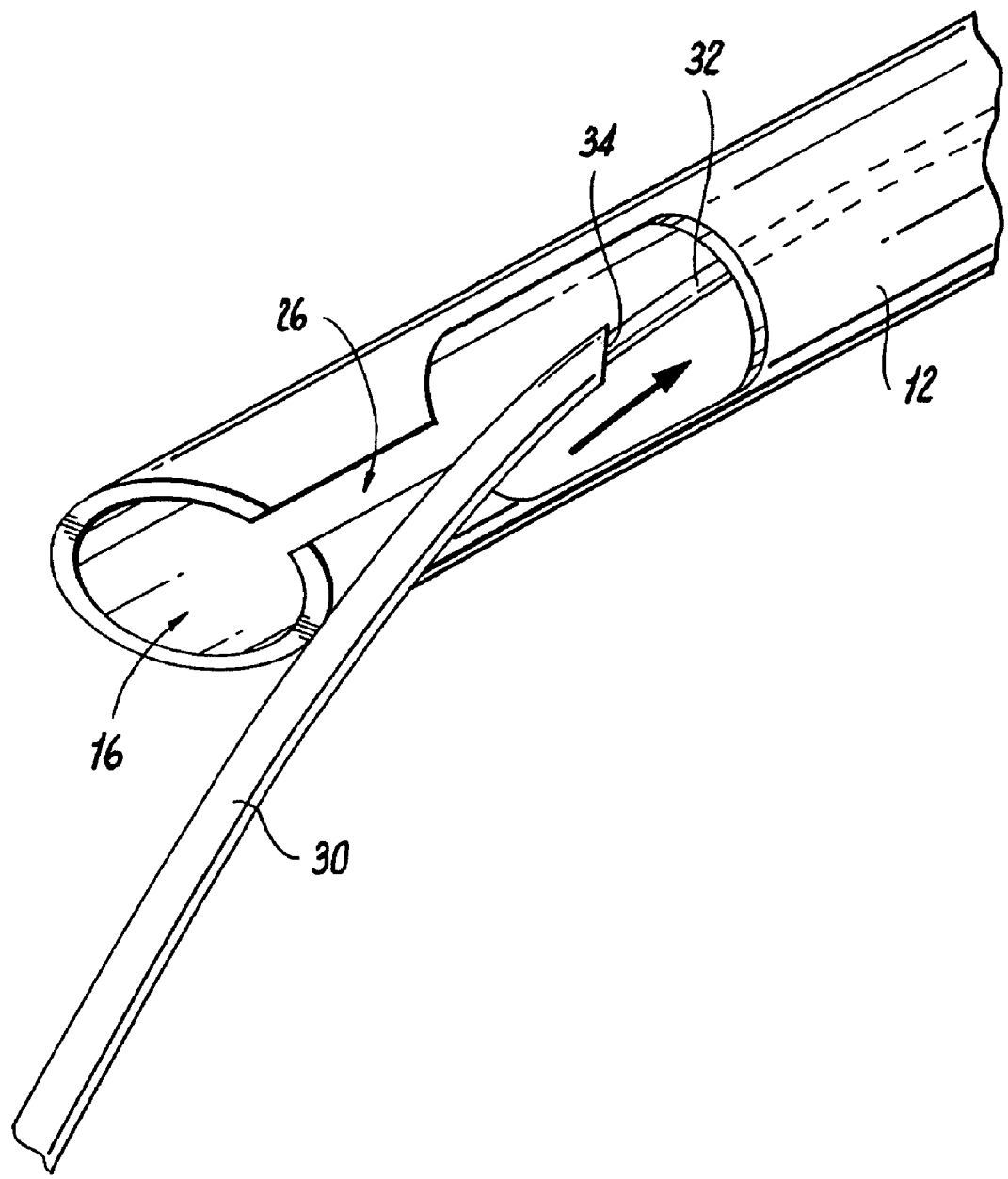
FIG. 2 is a view illustrating additional components of the system utilized with the access device of FIG. 1 to perform the colostomy reversal procedure.

Referring now to FIG. 2, there is illustrated additional surgical instrumentation of the system utilized to perform the method in accordance with the principles of the present disclosure. This instrumentation includes needle 30 and guide wire 32. Needle 30 is preferably a cannulated needle having a distal beveled edge 34 for incising tissue. Cannulated needle 30 preferable defines an inner bore or cannulation for reception and passage of the guide wire 32. Guide wire 32 may be any suitable guide wire having sufficient flexibility for maneuvering within tissue.

Figure 3:
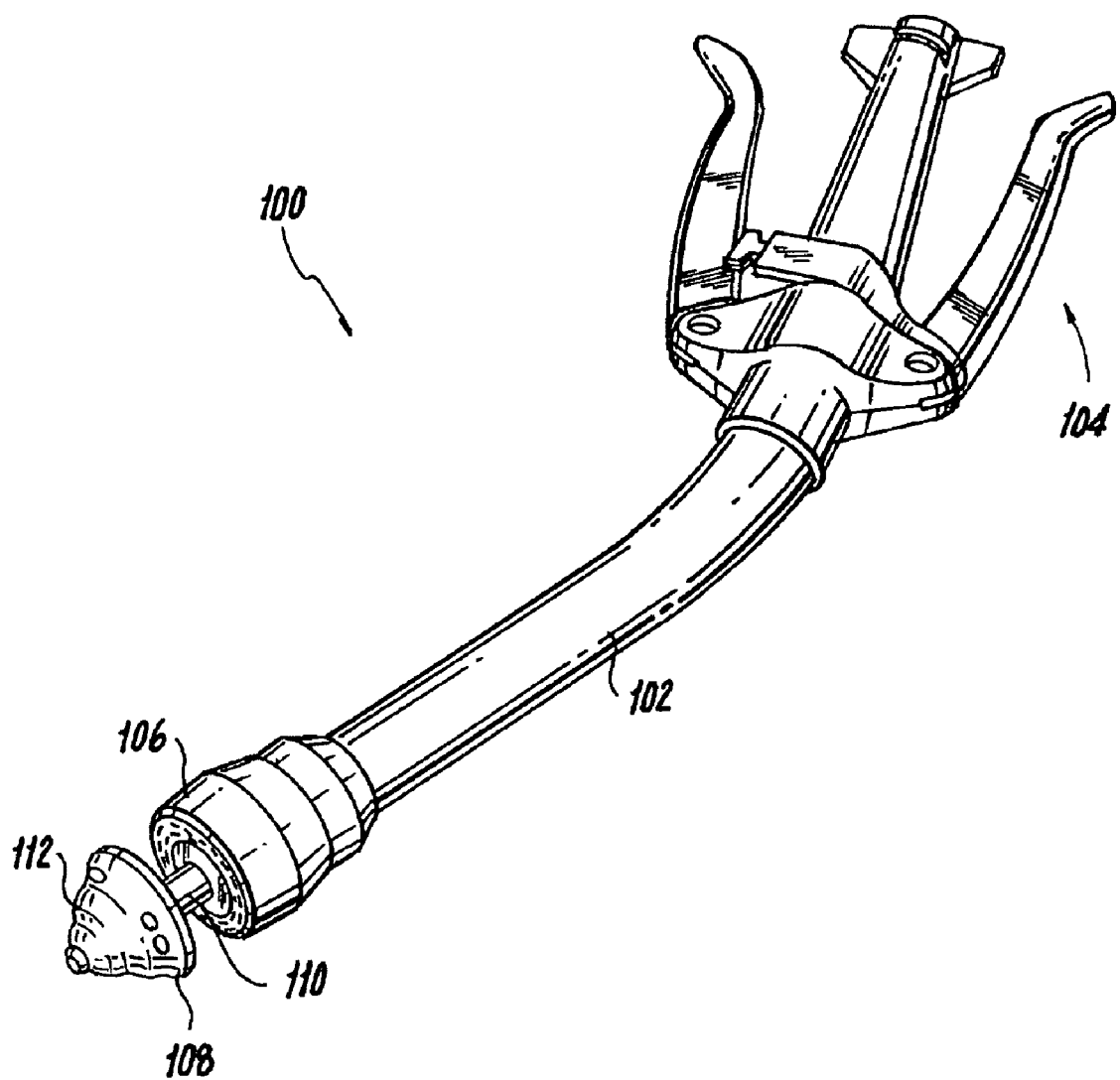
FIG. 3 is a perspective view of an end to end anastomosis instrument.

FIG. 3 illustrates a circular or end to end anastomosis instrument which is utilized to perform the procedure of the present disclosure. This instrument 100 is marketed under the name PREMIUM CEEA™ manufactured by U.S. Surgical Corporation, of Norwalk, Conn. and is the subject of commonly assigned U.S. Pat. No. 5,119,983, the contents of which are incorporated herein by reference. This instrument 100 includes an elongated shaft 102 having a handle portion 104 at a proximal end to actuate the instrument and a staple holding component 106 disposed at a distal end. An anvil component 108 is detachably mounted to the distal end of elongated shaft 102 by a mounting mechanism within the shaft which cooperatively engages the anvil component. Anvil component 108 includes anvil rod 110 with attached anvil head 112. Anvil head 112 includes staple receiving buckets (not shown) to receive the staples expelled by the staple firing mechanism to clinch the staples and effect joining of the adjacent tissue sections. One anvil suitable for the purposes of the present disclosure is disclosed in commonly assigned U.S. Pat. No. 5,718,360 to Green et al., the contents of which are incorporated herein by reference.

In use of instrument 100, opposed end portions of the organs to be stapled are clamped between the anvil head 112 and the staple holding component 106. The clamped tissue is stapled by driving one or more staples from the staple holding component 106 so that the ends of the staples pass through the tissue and are clinched by the anvil head 112. In some applications of the circular anastomosis procedure, the anvil rod 110 with attached anvil head 112 is mounted to the distal end of the shaft 102 prior to insertion of the instrument into the tissue to be anatomized. However, in other applications and in accordance with the preferred method of the present disclosure, it is preferable to utilize a detachable anvil which may be mounted to the instrument subsequent to positioning of the instrument and the anvil component within their respective tissue sections. In such instances, the stapling instrument and the anvil 108 are separately applied to the operative site. Each tissue section is then secured to their respective anvil 108 or staple holding component 106 by, e.g., a purse string stitch. The anvil 108 is mounted to the surgical instrument by inserting anvil rod 110 of the anvil 108 within the distal end of the instrument so that a mounting mechanism within the instrument securely engages the rod 110.

Colostomy Procedure

Figure 4:
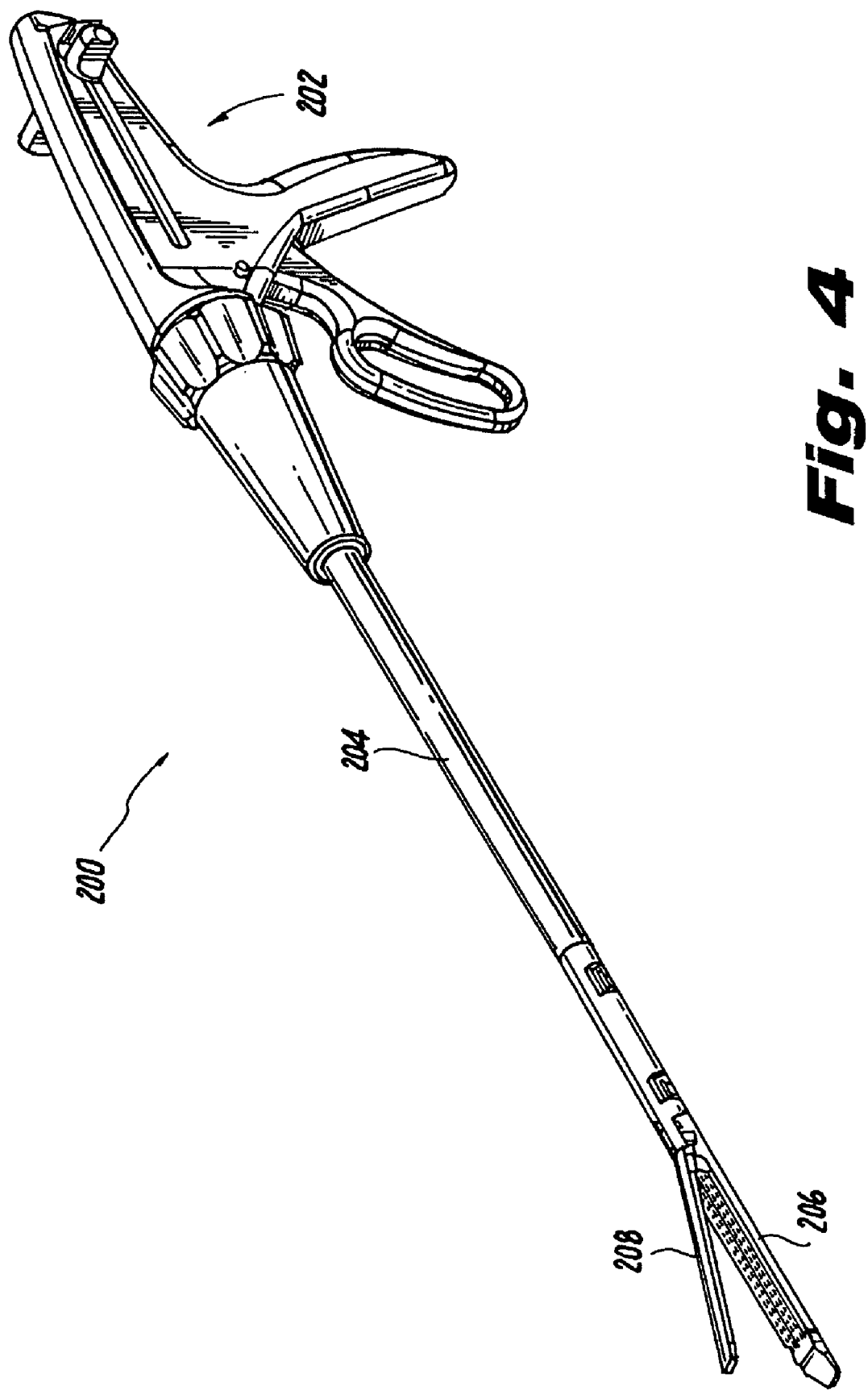
FIG. 4 is a perspective view of a surgical stapling apparatus that can be used in performing the colostomy reversal procedure.

A preferred colostomy procedure is known as a laparoscopic Hartmann procedure generally described in the background of this application. The Hartmann procedure involves resecting a diseased colon portion and rerouting the healthy proximal tract or colon through an opening or stoma in the abdominal wall leaving the distal bowel section connected to the rectum. The end of the healthy colon is preferably folded back to receive sutures which pass through the folded areas for attachment to the abdominal wall. The preferred Hartmann procedure is preferably performed under laparoscopic conditions which involve insufflating the peritoneal cavity with insufflation gases to raise the cavity wall to provide enhanced access therein. The diseased colon is resected preferably with a surgical stapling apparatus which is introduced through a trocar accessing the abdominal cavity. One suitable apparatus is marketed under the tradename ENDO GIA™ by U.S. Surgical Corporation of Norwalk, Conn. and is depicted in FIG. 4. This instrument is the subject of commonly assigned U.S. Pat. No. 5,894,979, the contents of which are incorporated herein by reference. This instrument 200 is adapted to place a plurality of longitudinal or linear rows of staples and may further include a knife for making an incision in body tissue between the rows of staples. The instrument 200 includes a frame 202 and an elongated tubular member 204 mounted to the frame 202. Mounted to the distal end portion of the tubular member is a cartridge assembly 206 which houses a plurality of rows of staples. An anvil 208 is pivotably movable relative to the cartridge assembly 206 to position tissue therebetween. Upon activation, the staples are fired to be clinched by the anvil 208 while the knife severs the tissue between the adjacent rows of staples This instrument fires a linear row(s) of staples through the colon. A knife blade incorporated within the instrument removes or severs the tissue adjacent the staple line thus detaching the diseased colon section from the lower or bowel section of the intestinal tract. As appreciated, however, the end of the bowel section or rectal stump removed from the anal opening is closed via the staple line.

Figure 5:
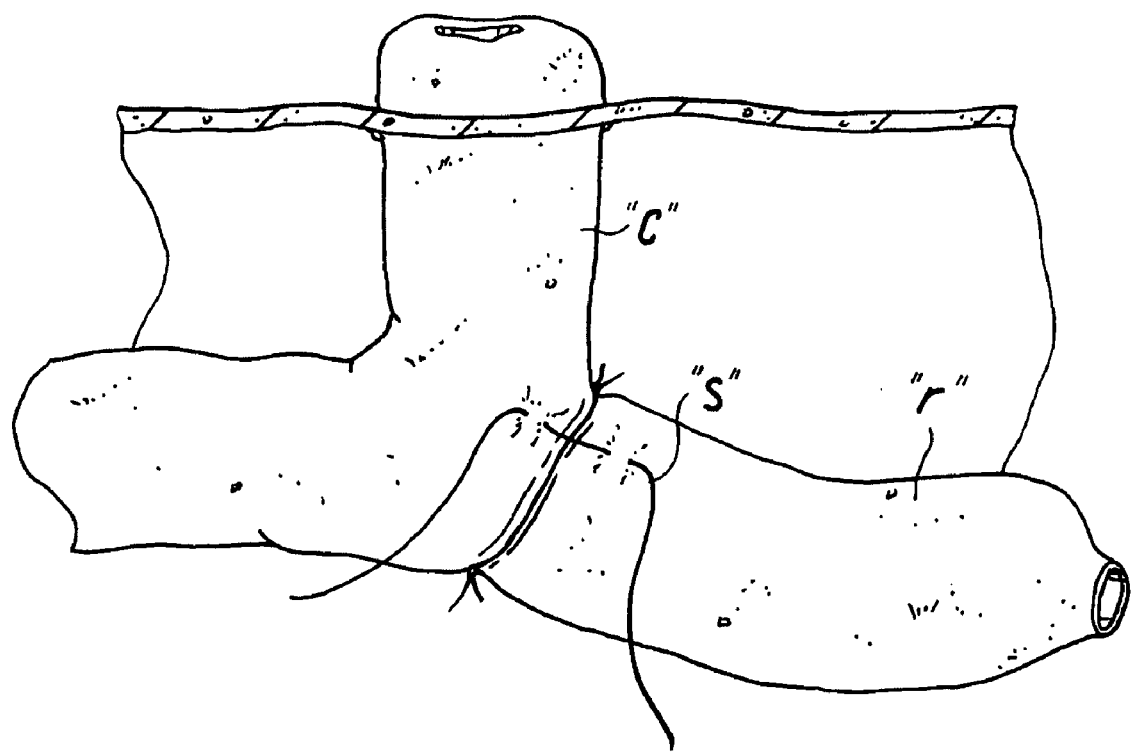

With reference now to FIG. 5, as part of the Hartmann procedure, the rectal or bowel stump "r" may be re-approximated to the surface of the colon section adjacent the end colostomy. This is accomplished by suturing the stapled end of the rectal stump to the serosal surface of the colon "c" at a location displaced from the anterior abdominal wall. A plurality of circumferentially displaced sutures "s" may be used to secure this re-approximation. Fluoroscopy may be utilized to confirm the re-approximation. Alternatively, this step may be performed during the colostomy reversal procedure.

Endoluminal Colostomy Reversal Procedure

Figure 6:
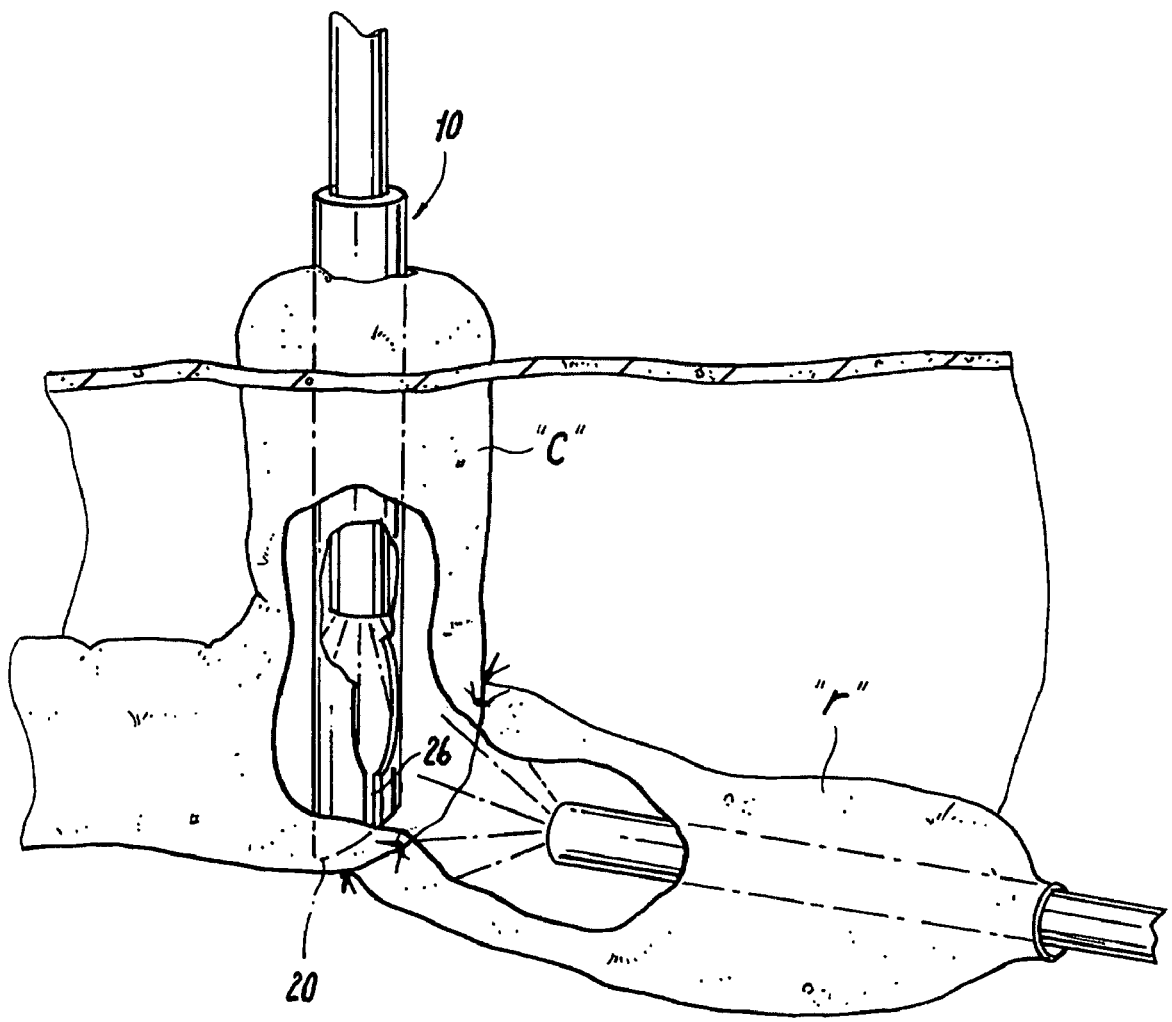

After a period of healing, attention is directed to performing the novel colostomy reversal procedure. At this point, if the rectal stump was not re-approximated during the colostomy procedure, re-approximation is effected in the aforedescribed manner. The abdominal cavity is insufflated via known techniques. With reference now to FIG. 6, initially, access device 10 is introduced within the stoma opening and advanced whereby the distal end 20 is adjacent the reapproximation location with window 24 of access device 10 arranged to face the rectal stump "r". Upon insertion, access device 10 serves as a stabilizing device. Specifically, the lumen of the end colostomy limb or colon "c" is often collapsed, so as to assist in maintaining patency. The access device is advantageously configured to open and stabilize the lumen upon its introduction within the healthy colon "c". Thereafter, two endoscopes (e.g., one rigid sigmoidoscope and one flexible endoscope) are inserted into the rectum and the end-colostomy respectively to obtain clear images of both sides of the future anastomosis. One suitable endoscope or laparoscope is disclosed in U.S. Pat. No. 5,954,637 to Francis, the contents of which are incorporated herein by reference. The endoscope is preferably equipped with an inclined angle of view and is positioned to a location where the distal end of the scope is adjacent the window 24 to permit visualization of the interior wall of the colon "c". With simultaneous views obtained of the end colostomy lumen and the stapled end of the rectal stump or Hartmann pouch, a "zone-of-safety" is determined to identify the site of the future anastomosis.

Figure 7:
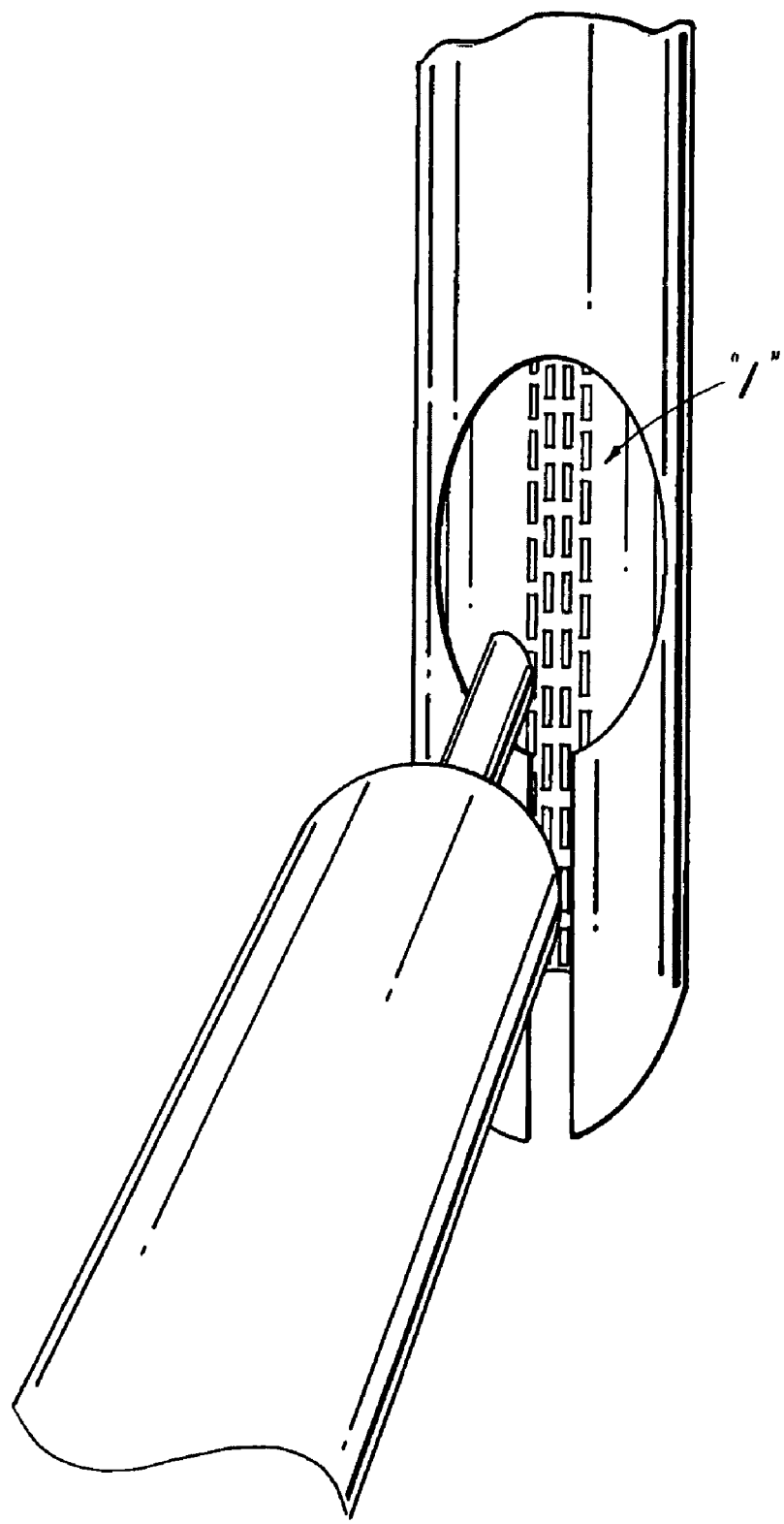
Figure 8:
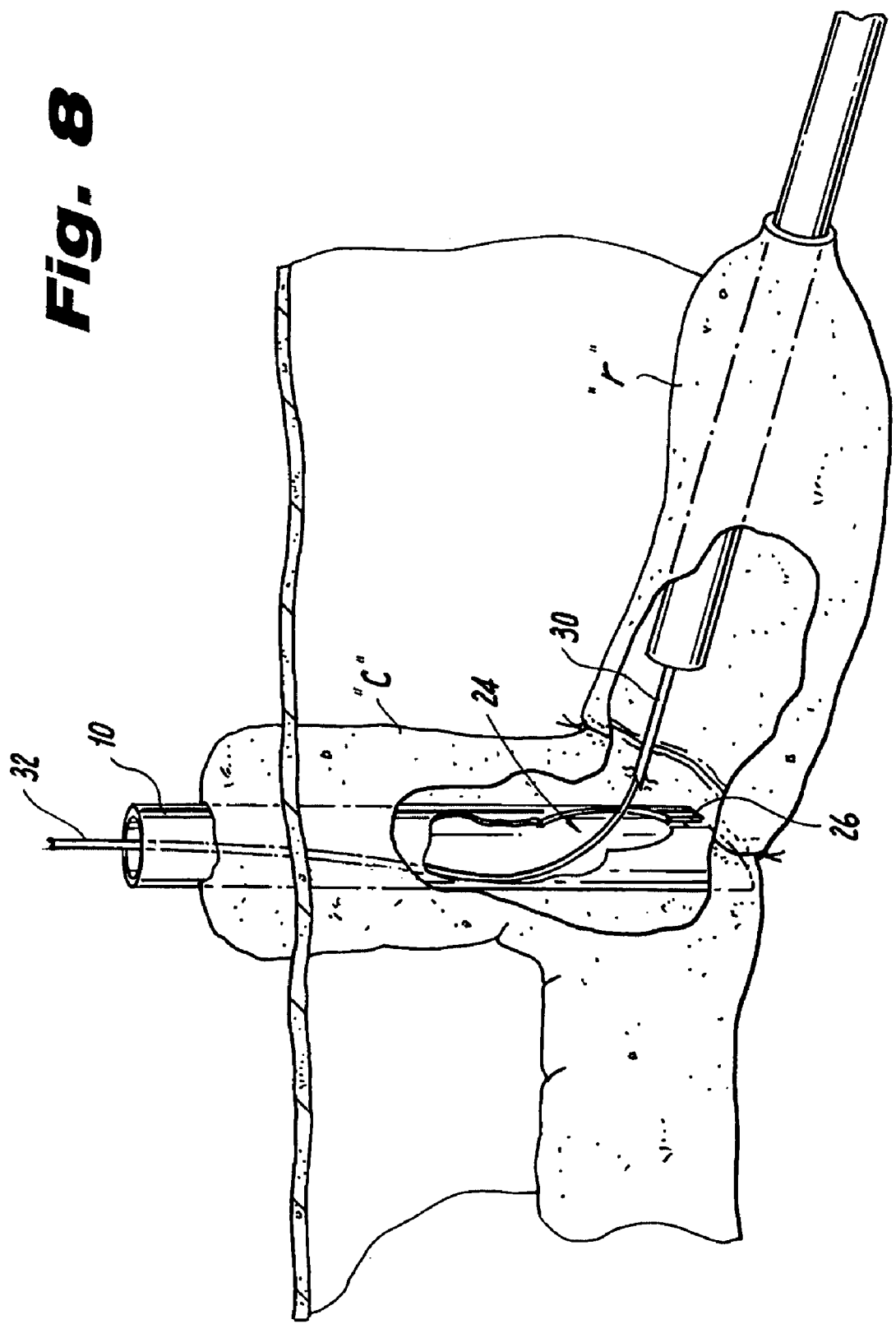
Figure 10:
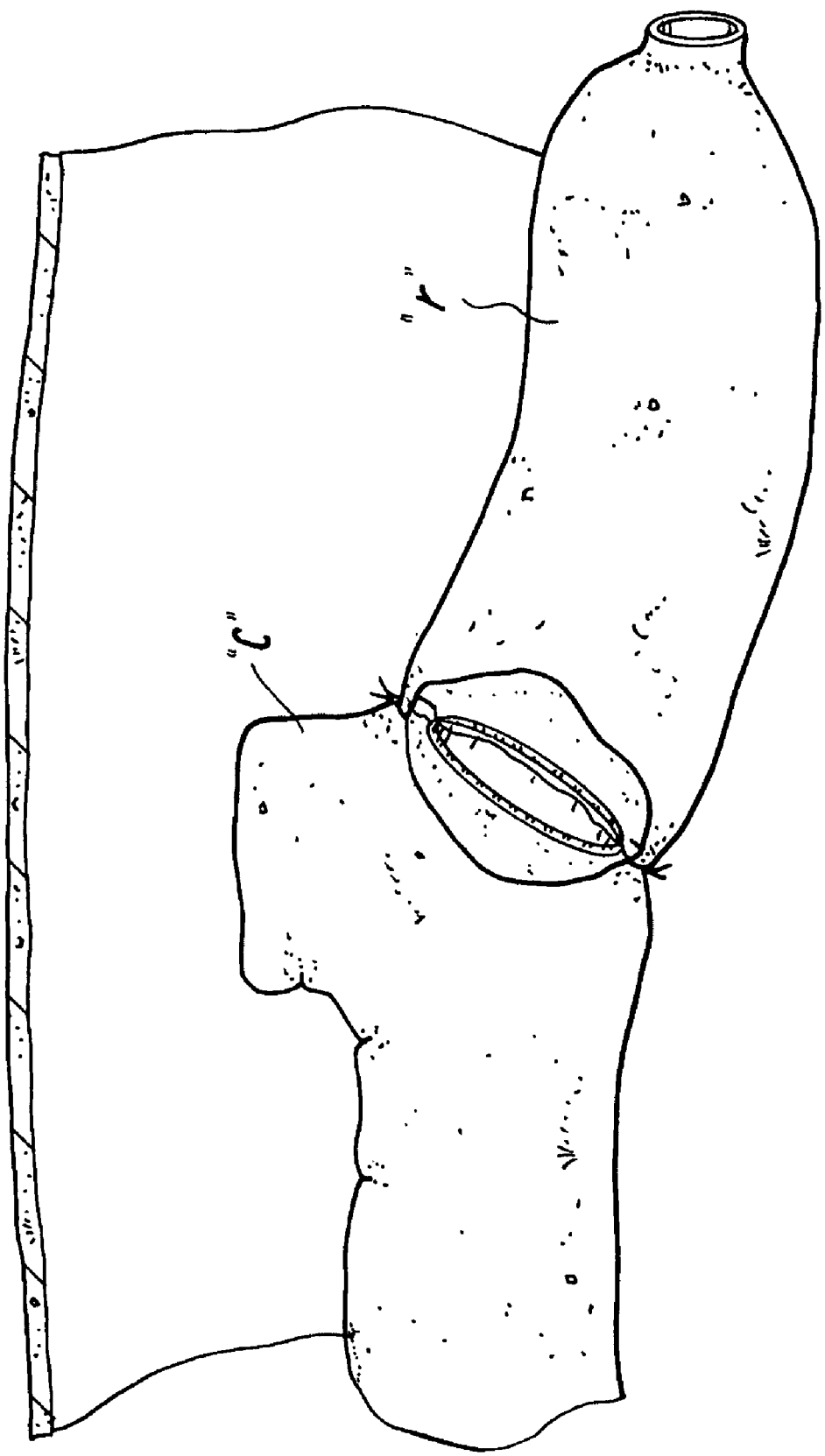

With reference to FIGS. 7 and 8, needle 30 is introduced through the sigmoidoscope until the beveled edge 34 presses against the stapled tissue area. Using dual imaging provided by the scopes, the surgeon monitors movement of the needle edge 34 on the tissue on the rectal stump side. Once location of the needle 30 is confirmed, the needle 30 is advanced through the tissue to form a puncture hole adjacent the staple line "l" to establish communication between the lumen of the rectal stump "r" and the lumen of the healthy colon "c". The endoscope is then withdrawn from access device 10.

As best depicted in FIG. 8, guide wire is advanced through cannulated needle 30 and extends through window 24 of access device 10 to enter the lumen of the access device 10. During insertion through the window 24, the guide wire 32 is eventually engaged by the inner wall portion of access device 10 opposed to window 24 and continues to run along the lumen of the access device 10 for exposure outside the body. By virtue of the positioning of window 24, guide wire 32 may be safely inserted through the colon tissue with minimal potential of any undesired penetration into the colon, i.e., the guide wire 32 is confined within the window 24 and lumen of access device 10 during insertion and advancement into the healthy colon. The guide wire 32 is continually advanced through access device until the tip of the guide wire 32 is passed out the colostomy. Access device 10 is then removed. During removal of the access device 10, the guide wire 32 traverses the slot 26 in the access device to be in general alignment with the longitudinal bore 16. This facilitates removal of the access device along the guide wire 32.

Referring to FIG. 9, an anvil 108 of the type aforedescribed in connection with FIG. 3 is connected to the exposed end of the guide wire. The anvil 108 may be connected to the guide wire 32 with sutures "v", e.g., passed through an opening in the anvil rod. Other means for connecting the anvil 108 to the guide wire 32 are also envisioned. Thereafter, the guide wire 32 is withdrawn from the rectal stump "r" thus pulling the anvil 108 through the proximal colon section for positioning the anvil adjacent the future colostomy site as depicted in FIG. 9. It is appreciated that the anvil rod of the anvil 108 must be introduced through the puncture openings in the healthy colon and rectal stump. This may be facilitated with the use of forceps introduced through a strategically positioned trocar or through the rectal opening. Additionally, the suture "v" attached to anvil 108 may be grasped and manipulated to orient the anvil at the desired location. The rigid sigmoidoscope is removed. A circular stapler instrument of the type described in connection with FIG. 3 is then introduced through the rectal opening. The anvil 108 is thereafter connected to the circular stapler instrument 100. Once together, the tissue is approximated and the stapler is fired. Firing of the stapler attaches the rectal stump "r" with the healthy colon "c" and redefines the path through the intestinal tract and out the rectum. As appreciated, a circular knife blade within the circular stapler instrument cuts a circular opening through the respective tissue upon firing. Alternatively, the stapler may be devoid of a circular knife blade whereby the coring step is performed manually with a scalpel. FIG. 9 illustrates the reestablished continuity of the intestines. The connection is inspected for completion and an endoscope is inserted transanally to inspect the integrity of the anastomosis. Finally, the end colostomy is removed or taken down and the stoma opening is closed.

It will be understood that various modifications may be made to the embodiments disclosed herein. Therefore, the above description should not be construed as limiting, but merely as exemplifications of preferred embodiments. For example, it is envisioned that the procedure has application in other reversing other colostomy procedures such as a double barrel colostomy (involving the formation of two separate stomas in the abdominal wall) and/or loop colostomy (involving bringing a loop of a colon section out the opening in the colon wall and making an incision in the colon to allow drainage of feces). It is also contemplated that the access device can be inserted in the second or distal intestinal section through the rectal opening and the procedure reversed. Those skilled in the art will envision other modifications within the scope and spirit of the claims appended hereto.

What is claimed is:

1. An endoluminal protection and access device for positioning within a lumen of a gastrointestinal tract, which comprises:

an access member including an outer wall defining an internal lumen, the access member having a longitudinal axis and proximal and distal ends, the distal end being sufficiently blunt to prevent perforation of the gastrointestinal lumen during positioning of the device, the outer wall defining a window through an entire thickness of the outer wall in a radial direction, wherein the window is adjacent the distal end and in communication with the internal lumen and has a radial arc ranging from about 90 degrees to about 180 degrees around the longitudinal axis,
the outer wall defining a slot through the entire thickness of the outer wall in the radial direction,
wherein the slot extends from the window to the distal end of the access member and has a radial arc around the longitudinal axis that is smaller than the radial arc of the window,
the outer wall further having a continuous circumference forming an enclosed cylindrical section from the window to the proximal end, the access member having a cross-sectional dimension transverse to the longitudinal axis and a rigidity and a size of the cross-sectional dimension sufficient to stabilize the gastrointestinal lumen upon positioning therein to maintain patency of the gastrointestinal lumen,
wherein the access member is sufficiently flexible to permit navigation through a tortuous path.

2. The endoluminal protection and access device according to claim 1, including a housing mounted to the access member for facilitating manipulation about an operative site, the housing having ports for the ingress and egress of insufflation gases.

3. The endoluminal protection and access device according to claim 1 wherein the window has a longitudinal dimension greater than or equal to a linear dimension of the window defined by the radial arc in the outer wall.

4. The endoluminal protection and access device according to claim 1 wherein the slot extends to the distal end of the access member through less than one revolution of a circumference of the outer wall.

5. The endoluminal protection and access device according to claim 1 wherein the slot extends parallel to the longitudinal axis to the distal end of the access member.

6. The endoluminal protection and access device according to claim 1 wherein the slot has a length along the longitudinal axis of the access member less than a length of the window along the longitudinal axis of the access member.

7. The endoluminal protection and access device according to claim 1 wherein the access member is made of medical grade material.

8. The endoluminal protection and access device according to claim 1 wherein the access member is sufficiently flexible to permit navigation through a gastrointestinal tract.

9. The endoluminal protection and access device according to claim 1, including a housing mounted on the proximal end of the access member and configured to provide insufflation gases through the internal lumen to raise a wall of the gastrointestinal tract.

10. The endoluminal protection and access device of claim 1 further comprising an opening at the distal end of the access member,
wherein the opening intersects the longitudinal axis of the access member, and
wherein the slot extends from the window to the opening at the distal end of the access member.

11. The endoluminal protection and access device of claim 10 wherein the outer wall includes one and only one window and one and only one slot, wherein the one and only one slot extends from the one and only one window to the opening at the distal end of the access member.

12. An endoluminal mucosal protection and lumen stabilizing device, comprising:
an elongated access member made of medical grade material and having a proximate end, a distal end and an outer wall defining a longitudinal bore extending the length of the access member;
the outer wall having a window communicating with the longitudinal bore, the window having a radial arc in the range of about 90 degrees to about 180 degrees around a longitudinal axis of the access member, wherein the window extends through an entire thickness of the outer wall in a radial direction;
the outer wall having a slot communicating with the longitudinal bore and extending from the window to the distal end approximately parallel to the longitudinal axis of the access member, wherein the slot extends through the entire thickness of the outer wall in the radial direction and defines a radial arc around the longitudinal axis that is smaller than the radial arc of the window;
the outer wall being continuous and uninterrupted from the proximate end to the window so as to form an enclosed passageway for insufflation gases; and
the distal end of the access member being formed so as to minimize perforation of a body lumen,
wherein the access member is sufficiently flexible to permit navigation through a tortuous path.

13. The endoluminal mucosal protection and lumen stabilizing device of claim 12, further comprising a housing mounted to the access member for facilitating manipulation about an operative site.

14. The endoluminal mucosal protection and lumen stabilizing device of claim 12, further comprising a housing mounted on the proximal end of the access member that is configured to provide insufflation gases through the internal lumen to raise a wall of the gastrointestinal tract.

15. The endoluminal mucosal protection and lumen stabilizing device of claim 12, wherein the access member is sufficiently flexible to permit navigation through a gastrointestinal tract.

16. An endoluminal mucosal protection and lumen stabilizing device, comprising:
an elongated access member made of medical grade material and having a proximate end, a distal end and an outer wall defining a longitudinal bore extending the length of the access member;
the outer wall having a window communicating with the longitudinal bore and defining a radial arc in the range of about 90 degrees to about 180 degrees around a longitudinal axis of the access member;
the outer wall having a slot that extends through an entire thickness of the outer wall and communicating with the longitudinal bore, wherein the slot extends from the window to the distal end approximately parallel to the longitudinal axis of the access member;
the outer wall having a circumferentially uninterrupted longitudinal bore from the window to the proximate end;
a cannula housing having ports that allow insufflation and desufflation of biologically non-reactive gases in and out of the elongated access member;
the elongated access member being removably attachable to the cannula housing; and
the distal end of the access member being formed so as to minimize perforation of a body lumen,
wherein the access device is flexible to permit navigation through a tortuous path.

17. An endoluminal protection and access device for positioning within a lumen of a gastrointestinal tract, the device comprising:

an access member including an outer wall defining an internal lumen, the access member having a longitudinal axis and proximal and distal ends, the distal end being sufficiently blunt to prevent perforation of the gastrointestinal lumen during positioning in the gastrointestinal lumen, an opening at the distal end of the access member, wherein the opening intersects the longitudinal axis of the access member, a window that extends through the entire thickness of the outer wall in a radial direction adjacent the distal end of the access member, the window having a radial arc ranging from about 90 degrees to about 180 degrees around the longitudinal axis, the outer wall further having a continuous circumference forming an enclosed cylindrical section from the window to the proximal end, the access member having a cross-sectional dimension transverse to the longitudinal axis and a rigidity and a size of the cross-sectional dimension sufficient to stabilize the gastrointestinal lumen upon positioning therein to maintain patency of the gastrointestinal lumen, wherein the access member is sufficiently flexible to permit navigation through a tortuous path, wherein the endoluminal protection and access device further comprises a slot through the entire thickness of the outer wall in the radial direction, wherein the slot extends in a longitudinal direction from the window to the opening at the distal end of the access member, wherein the slot has a radial arc that is less than the radial arc of the window around the longitudinal axis.

18. The endoluminal protection and access of claim 17 including one and only one window and one and only one slot.

19. An endoluminal protection and access device for positioning within a lumen of a gastrointestinal tract, the device comprising:

an access member including an outer wall defining an internal lumen, the access member having a longitudinal axis and proximal and distal ends, the distal end being sufficiently blunt to prevent perforation of the gastrointestinal lumen during positioning in the gastrointestinal lumen, an opening at the distal end of the access member, wherein the opening intersects the longitudinal axis of the access member, one and only one window in the outer wall that extends through the entire thickness of the outer wall in a radial direction and is adjacent the distal end of the access member, the window having a radial arc around the longitudinal axis between about 90 degrees and about 180 degrees, one and only slot that extends through the entire thickness of the outer wall in the radial direction, wherein the slot extends in a longitudinal direction from the window to the opening at the distal end of the access member, wherein the slot has a radial arc around the longitudinal axis that is less than the radial arc of the window, the outer wall further having a continuous circumference forming an enclosed cylindrical section from the window to the proximal end, the access member having a cross-sectional dimension transverse to the longitudinal axis and a rigidity and a size of the cross-sectional dimension sufficient to stabilize the gastrointestinal lumen upon positioning therein to maintain patency of the gastrointestinal lumen, wherein the access member is sufficiently flexible to permit navigation through a tortuous path.

\* \* \* \* \*